(12) United States Patent
Stuermer et al.

(10) Patent No.: US 8,124,387 B2
(45) Date of Patent: Feb. 28, 2012

(54) PROCESS FOR THE PRODUCTION OF CITRONELLAL

(75) Inventors: Rainer Stuermer, Roedersheim-Gronau (DE); Thomas Friedrich, Darmstadt (DE); Andre Mueller, Vienna (AU); Bernhard Hauer, Fussgoenheim (DE); Bettina Rosche, Randwick (AU)

(73) Assignee: BASF SE, Ludwigshafen (DE)

( * ) Notice: Subject to any disclaimer, the term of this patent is extended or adjusted under 35 U.S.C. 154(b) by 958 days.

(21) Appl. No.: 12/093,796

(22) PCT Filed: Nov. 10, 2006

(86) PCT No.: PCT/EP2006/068338
§ 371 (c)(1),
(2), (4) Date: May 15, 2008

(87) PCT Pub. No.: WO2007/057354
PCT Pub. Date: May 24, 2007

(65) Prior Publication Data
US 2008/0280337 A1    Nov. 13, 2008

Related U.S. Application Data

(60) Provisional application No. 60/737,500, filed on Nov. 17, 2005.

(30) Foreign Application Priority Data

Nov. 17, 2005 (EP) .................................. 05110867

(51) Int. Cl.
*C12P 7/24* (2006.01)
(52) U.S. Cl. ... 435/147; 435/179; 435/171; 435/252.35; 435/252.4; 435/252.5
(58) Field of Classification Search .................. 435/147, 435/179, 171, 252.35
See application file for complete search history.

(56) References Cited

U.S. PATENT DOCUMENTS
4,237,072 A    12/1980  Aviron-Violet et al.

FOREIGN PATENT DOCUMENTS
EP    0000315 A1    1/1979
GB    1476818       6/1977

OTHER PUBLICATIONS

Chatterjee et al. Indian J.Chem. (1999) 38B: 1025-1029.*
Müller, A., et al., "Enzymatic Reduction of the α,β—Unsaturated Carbon Bond in Citral", Journal of Molecular Catalyst B: Enzymatic, 2006, vol. 38, pp. 126-130.
Williams, R. E., et al., "'New Uses for an Old Enzyme'—The Old Yellow Enzyme Family of Flavoenzymes", Microbiology, 2002, vol. 148, pp. 1607-1614.
Vaz, A. D. N., et al., "Old Yellow Enzyme: Aromatization of Cyclic Enones and the Mechanism of a Novel Dismutation Reaction", Biochemistry, 1995, vol. 34, pp. 4246-4256.
Kitzing, K., et al., "The 1.3 Å Crystal Structure of the Flavoprotein YqjM reveals a Novel Class of Old Yellow Enzymes", The Journal of Biological Chemistry, 2005, vol. 280, No. 30, 27904-27913.
Stott, K., et al., "Old Yellow Enzyme", The Journal of Biological Chemistry, 1993, vol, 268, No. 9, pp. 6097-6106.
Seo, J., et al., "The genome sequence of the ethanologenic bacterium Zymomonas mobilis ZM4", Nature Biotechnology, 2005, vol. 23, No. 1, p. 63.

* cited by examiner

*Primary Examiner* — Susan Hanley
(74) *Attorney, Agent, or Firm* — Connolly Bove Lodge & Hutz LLP

(57) ABSTRACT

The invention relates to a process for the production of optically active Citronellal by enzymatic reduction of Citral with a reductase from *Zymomonas mobilis*.

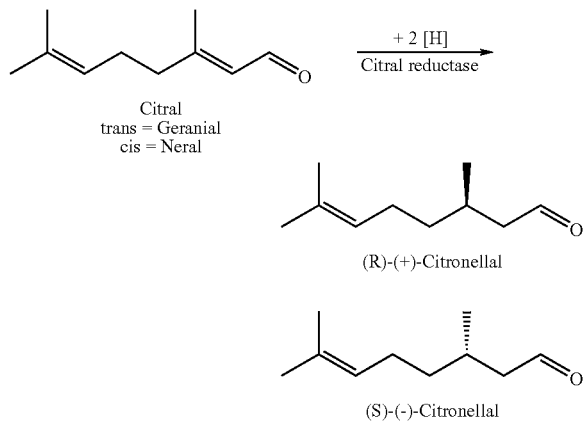

6 Claims, 4 Drawing Sheets

SEQUENCE LISTING

<160> NUMBER OF SEQ ID NOS: 1

<210> SEQ ID NO 1
<211> LENGTH: 27
<212> TYPE: PRT

```
<213> ORGANISM: Zymomonas mobilis

<400> SEQUENCE: 1

Pro Ser Leu Phe Asp Pro Ile Arg Phe Gly Ala Phe Thr Ala Lys Asn
1               5                   10                  15

Arg Ile Trp Met Ala Pro Leu Thr Arg Gly Arg
            20                  25
```

PROCESS FOR THE PRODUCTION OF CITRONELLAL

RELATED APPLICATIONS

This application is a national stage application (under 35 U.S.C. §371) of PCT/EP2006/068338, filed Nov. 10, 2006, which claims benefit of European application 05110867.8, filed Nov. 17, 2005, and U.S. Provisional Application Ser. No. 60/737,500, filed Nov. 17, 2005.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_00663_US. The size of the text file is 1 KB, and the text file was created on Jul. 12, 2011.

Citral is an antimicrobial terpene, which imparts the characteristic lemon scent to plants like lemon grass and the Australian lemon myrtle. It is also readily available as an industrial intermediate e.g. in the synthesis of the vitamins A and E. Several bioconversions of citral have been reported, viz. reduction or oxidation of the aldehyde group [1], acyloin formation [2] and lyase activity [1, 3].

The objective of this study was to screen for enzyme activities which reduce the α,β-unsaturated carbon bond in citral to yield the chiral product citronellal (FIG. 1). Citral is a mixture of the trans-isomer geranial and the cis-isomer neral, but substrate specificity for either isomer might not be crucial as amino acids can catalyze the isomerization [4].

Figure 1:
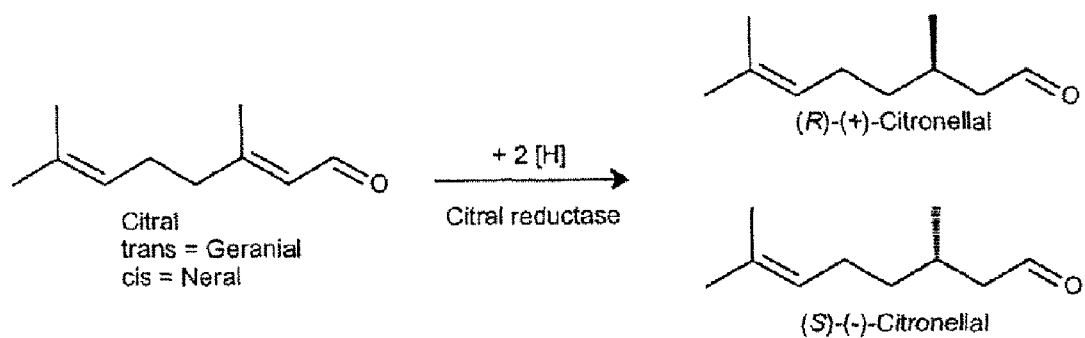
FIG. 1: Biotransformation of citral (geranial and neral) into citronellal.

A valuable use for the product (R)-(+)-citronellal is the subsequent ring closure via a Prins reaction into isopulegol followed by hydration to (IR,2S,5R)-(−)-menthol [5]. Non-biological strategies are still challenged by their limited stereo-selectivity (citral has three double bonds) and enantio-selectivity [6] (see FIG. 1)

Enzymes which reduce the carbon double bond of other α,β-unsaturated carbonyls have been reported in the literature. They predominantly belong to the 'Old Yellow Enzyme' family of flavin and NADPH dependant reductases, reviewed by Williams and Bruce [7] with regards to possible biotechnological applications.

Another example is carvone reductase from *Rhodococcus erythropolis*, which used an unidentified heat stable cofactor and was not dependant on added NADH or NADPH [8].

In order to detect a bioconversion of citral into citronellal, the corresponding enzyme must be active, electrons for reduction must be available, the very hydrophobic substrate citral must reach the enzyme in sufficient concentrations and the citronellal formation must be faster than any subsequent conversion. Accordingly, a screening strategy was developed to test various microorganisms for citral conversion.

A first embodiment of the invention is a process for the production of optically active Citronellal by enzymatic reduction of Citral with a reductase which is selected from the group consisting of the genera *Zymomonas, Citrobacter, Candida, Saccharomyces, Kluyveromyces, Candida, Issatchenkia, Rhizopus* wherein the reduction is accomplished in a two-phase liquid system.

A preferred embodiment of this process uses a reductase selected from the species *Zymomonas mobilis, Citrobacter freundii, Candida rugosa, Saccharomyces bayanus, Saccharomyces cerevisiae, Kluyveromyces marxianus, Candida utilis, Issatchenkia orientalis, Rhizopus javanicus*.

The microorganisms mentioned above are well known in the art and can be isolated by known procedures or from public depositories such as ATCC and DSMZ.

*Zymomonas mobilis* has been deposited i.a. as ATCC 10998, ATCC 29192, ATCC 31821, ATCC 35001, ATCC 39985. *Citrobacter freundii* has been deposited i.a. as ATCC 8090D, ATCC 11811. *Candida rugosa* has been deposited i.a. as DSM 70761. *Issatchenkia orientalis* has been deposited i.a. as DSM 3433, DSM 6128, DSM 11956, DSM 70075, 70079.

The reductase can be used in an isolated and purified form or as a "whole-cell-enzyme" which shall mean, that the enzyme together with the microorganism is used for the process according to the invention. The microorganism can also be permeabilized in order to improve the substrate, product, cofactor transfer in and out of the cell.

The term "reductase" shall mean not only the isolated enzyme but also extracts, solutions or suspensions comprising the enzyme, carrier where the enzyme has been immobilized and whole cells containing the enzyme.

An improved embodiment of the invention is the use of a cofactor which is oxidized by the simultaneous reduction of Citral. As a cofactor every substance which can be oxidized under the conditions of the process according to the invention is suitable.

A preferred cofactor-system is NADH or NADPH which can be used in equimolar or even higher amounts or which can be regenerated by known systems, such as electrochemical means or an enzymatic regenerating system, such as the Glucose-6-phosphate-dehydrogenase. If the cofactor is regenerated amounts less than equimolar are preferred in the process.

A two-phase liquid system means a system which contains two liquid phases which do not mix with each other in a larger extent. Preferred is a two-phase liquid system wherein one phase contains an organic liquid and the second phase contains water or a water-based solvent. More preferred is a two-phase liquid system wherein the organic phase consists of ether such as ethylether, methyl-tert. butylether (MTBE) or aromatic carbohydrogens such as benzene and toluene. As the second liquid phase a buffered aqueous solution is preferred.

The present invention investigates a biological strategy for the stereo- and enantio-specific reduction of the α,β-unsaturated carbon bond of the terpene citral (isomers geranial and neral) to citronellal. The traditional aqueous screening of 46 prokaryotic and eukaryotic microorganisms revealed only the gram-negative bacterium *Zymomonas mobilis* as capable of forming citronellal. A drawback of the aqueous system was the low solubility of the substrate citral in the aqueous medium.

In the two-phase biotransformation systems with cells of *Zymomonas mobilis*, up to ten times higher concentrations of citronellal were formed than in a system without added organic solvent. Best results were achieved with the organic solvents toluene, methyl tertiary-butylether (MTBE), isoamylalcohol and diethylether. Organic media in biocatalytic reactions with whole cells offer several advantages [9]. One benefit is an enhanced solubility of substrates and/or products. The organic phase allows high overall concentrations of the substrate in the reaction while maintaining low levels of toxic or inhibitory compounds in the aqueous phase. Permeabilization of the cells is another benefit of organic solvents. Besides 'freezing and thawing'-cycles, the use of organic solvents like toluene for permeabilization has been reported for many organisms, e.g. yeast *Kluyveromyces* [10] and *Zymomonas mobilis* [11], causing an increased passive flux over the cell membrane. The presence of EDTA can result in a significant increase in permeability of the outer membrane, as was demonstrated for *Escherichia coli* [12].

Using 20% [v/v] toluene or MTBE as organic solvent, 10 formerly negative tested strains out of the 46 proved positive. In comparison with the aqueous system this approach represented a far more successful strategy in screening potential microorganisms for the bioconversion of citral to citronellal. Highest product concentrations were obtained for the prokaryotic strains *Zymomonas mobilis* and *Citrobacter freundii* with enantiomeric excess values (e.e.) of >99% and 75% for the (S)-enantiomer, respectively. In contrast the eukaryotic strains showed opposite enantio-specificity with e.e. values of more than 98%, 97% and 96% for the (R) enantiomer with *Candida rugosa, Saccharomyces bayanus* and *Saccharomyces cerevisae*, respectively.

One problem encountered in bioconversions using whole cells is the formation of by-products due to numerous catalysts within the cells. Interestingly, most organic solvents tested with *Zymomonas mobilis* caused an overall decrease of the alcohol by-products geraniol, nerol and citronellol. Similarly EDTA decreased alcohol formation for both pro- and eukaryotic strains and in most cases increased citronellal concentrations. These opposite effects on product and by-product formation might indicate that the reduction of the aldehyde group and the reduction of the carbon double-bond in citral are catalyzed by different enzymes.

Enzymatic reductions of the double bond in α,β-unsaturated carbonyls have been described. In particular oxidoreductases of the "old yellow enzyme (OYE)"-family, flavin dependant enzymes common in yeasts, plants and bacteria [13], accept a large number of α,β-unsaturated aldehydes and ketones [7, 14, 15]. However conversion of citral by OYE has not been reported. A BLAST P (www.ncbi.nlm.nih.gov) search of the yeast OYE 1, 2 and 3 protein sequences was performed against the translated open reading frames of the recently published *Zymomonas mobilis* ZM4 genome [16]. Closest similarity was observed for a putative NADH: flavin oxidoreductase (ZM01885) with unknown function. However, the amino acid similarity to yeast OYEs was less than 50%. Whether or not citronellal formation is related to enzymes of the OYE family is not known yet and the overexpression of the corresponding genes will be required for the development of a high productivity bioprocess.

Experimental

Microbial Cultures

The 20 yeast strains, 9 strains of filamentous fungi and 17 bacterial strains were obtained from the University of New South Wales culture collection (World Culture Collection number 248). Yeast strains, filamentous fungi, and the bacteria *Zymomonas mobilis* and *Zymobacter palmae* were grown in YPG medium (3 g/l yeast extract, 5 g/l peptone, 10 g/l D-glucose, pH 6.9). Lactic acid bacteria were grown in MRS (de Man, Rogosa, Sharpe) broth from Oxoid (pH 6.2). Nutrient broth from Oxoid (pH 7.4) was used for all other bacteria. For *Planococcus citreus* and *Vibrio harveyi* nutrient broth was supplemented with 3% [w/v] NaCl. The growth temperature was 30° C. or 37° C., depending on which was closer to the reported optimal growth temperature. Cultures were agitated in an orbital shaker at 150 rpm except for non-agitated cultures of *Lactobacillus casei, Leuconostoc mesenteroides* and *Propionibacterium freundenreichii*. All cultures were grown to the stationary phase. For generating permeabilized cells, the biomass was washed twice in buffer (50 mM MOPS/KOH pH 7) and resuspended in half of the volume buffer (for yeast and filamentous fungi) or one quarter of the volume (bacterial cultures). The suspensions were freeze thawed three times using liquid nitrogen and a 25° C. water bath and were then stored in aliquots at −20° C.

Culture Screening in Aqueous Systems

Citral (5 mM) was added in form of a 0.2 M solution in isopropanol. The 2.5% [v/v] isopropanol fulfilled two functions: increasing the solubility of the hydrophobic substrate citral and potentially acting as a substrate for intracellular alcohol dehydrogenases to regenerate NAD(P)H. Each culture was subjected to three experiments.

Activity Assay (GC Assay for Determining the Citral Reductase Activity)

Procedure:

500 µl of sample or water (blank)
100 µl of 1M potassium phosphate, pH 7.0
100 µl of 1M glucose solution
100 µl of solution with in each case 10M NADPH/NADH
100 µl of glucose dehydrogenase *E. coli* cell suspension
25 µl of 10% cis/trans citral in DMSO Incubation: At least 15 h at 35° C., with vigorous shaking.
Extraction: To each sample 250 µl of chloroform are added and mixed well for at least 5 minutes. This is followed by centrifugation for 3 minutes. The lower organic phase is removed and dried on 4 A molecular sieve, transferred to HPLC glass vials with micro insets, measured by GC. The ee value for purified enzyme (estimated by comparing the areas) is over 98%.

a. Whole Cells in Culture Medium 5 ml of fresh medium were added to 5 ml of a stationary phase culture without change of temperature, agitated at 150 rpm for 1 h and then citral in isopropanol was added. After 3 h and after 24 h, 1 ml broth was extracted with 0.2 ml freshly prepared solution of 0.3% [v/v] 1-octanol (internal GC standard) in chloroform. The organic phase was recovered, diluted with isopropanol and analyzed by GC.

b. Permeabilized Cells+NADH 2 ml screw-cap glass vials agitated on an orbital shaker at 150 rpm and 30° C. contained 0.5 ml thawed permeabilized cells in a total volume of 1 ml, with final concentrations of 50 mM MOPS buffer at pH 7, 10 mM NADH, 5 mM citral and 2.5% [v/v] isopropanol. After 3 h the complete sample was extracted with chloroform/octanol as above.

c. Permeabilized Cells+NADPH Regenerating System

The procedure was the same as in b except that NADH was replaced by a NADPH regenerating system with final concentrations of 1.5 mM NADP+, 10 mM glucose-6-phosphate, 3.3 mM MgC12, and 0.4 U/ml glucose-6-phosphate dehydrogenase.

Culture Screening in a Two-Phase System

Prior to the biotransformation, 0.5 ml of permeabilized cells were vortexed with 0.15 ml toluene in 2 ml screw capped glass vials and incubated for 10 min at room temperature. The other components were then added to give 1 ml of aqueous phase with the same composition as the aqueous/NADPH system, with only citral and isopropanol omitted. The reaction was started by addition of 0.05 ml of 0.4 M citral in toluene and the vials were turned vertically on a wheel at 30° C. After 3 h the complete sample was extracted with 0.4 ml freshly prepared solution of 0.15% [v/v] 1-octanol (internal GC standard) in chloroform. After centrifugation 0.4 ml of the lower organic phase (toluene/chloroform mixture) was removed for GC analysis. Strains that formed citronellal were compared in a toluene and a methyl tertiary-butylether (MTBE) two-phase system as detailed below.

Biotransformations

Figure 2:
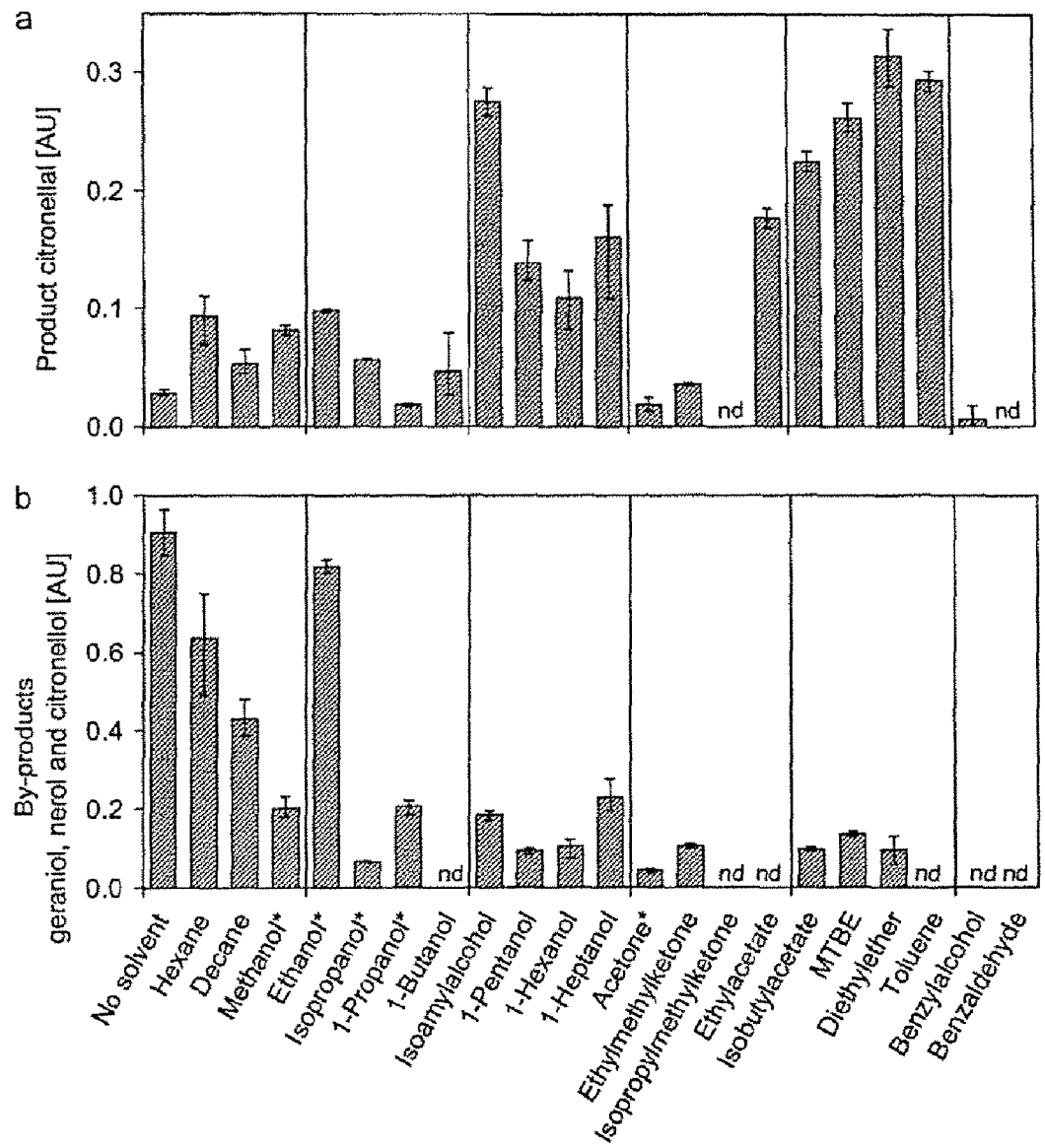
FIG. 2: Biotransformation of citral by *Zymomonas mobilis* cells in the presence of a NADPH regenerating system and various solvents: a) product citronellal b) sum of by-products geraniol, nerol and citronellol. Initial conditions: 20% v/v organic solvent, 20 mM citral, 5 mM dithiothreitol, 3.3 mM MgCl2, 1.5 mM NADP+, 10 mM glucose-6-phosphate, 0.4 U/ml glucose-6-phosphate dehydrogenase, approx. 14 g/l DCM Z. mobilis, 50 mM MOPS/KOH, pH 7.0, 3 h at 30° C. *Solvents marked with asterisk dissolved in water, all other solvents formed emulsions. MTBE=methyl tertiary butylether, nd=not detected. AU=arbitrary units: GC area of compound divided by the GC area of internal standard. Average values of three replicates are given and error bars indicate highest and lowest results. For toluene the ratio of areas corresponded to a co\-centration of 1.4 mM citronellal.
Figure 3:
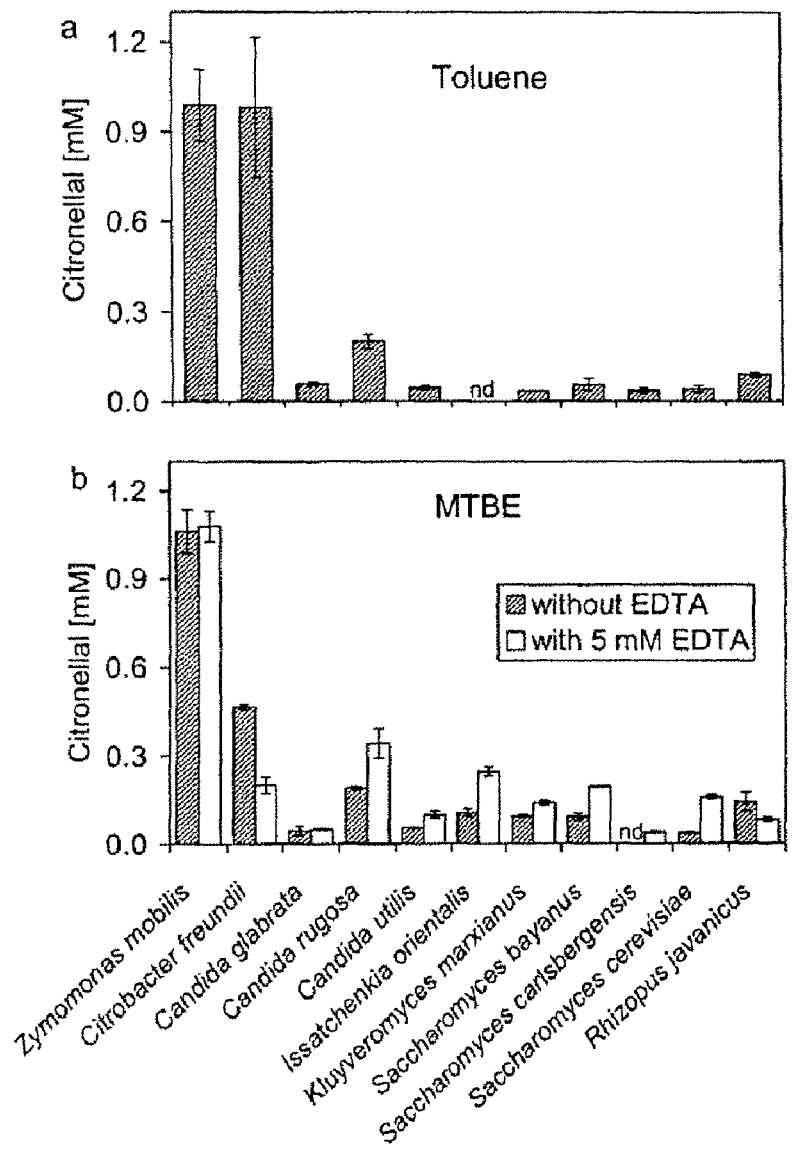
FIG. 3: Comparison of citronellal formation by bacteria, yeasts and a filamentous fungus in the a) aqueous/toluene two-phase system and b) aqueous/methyl tertiary butylether (MTBE) two-phase system (3 h incubation at 30° C., composition as in FIG. 2 at a biomass concentration of approximately 12 g DCM/l). Average values of two replicates are given and error bars indicate highest and lowest results, nd=not detected.
Figure 4:
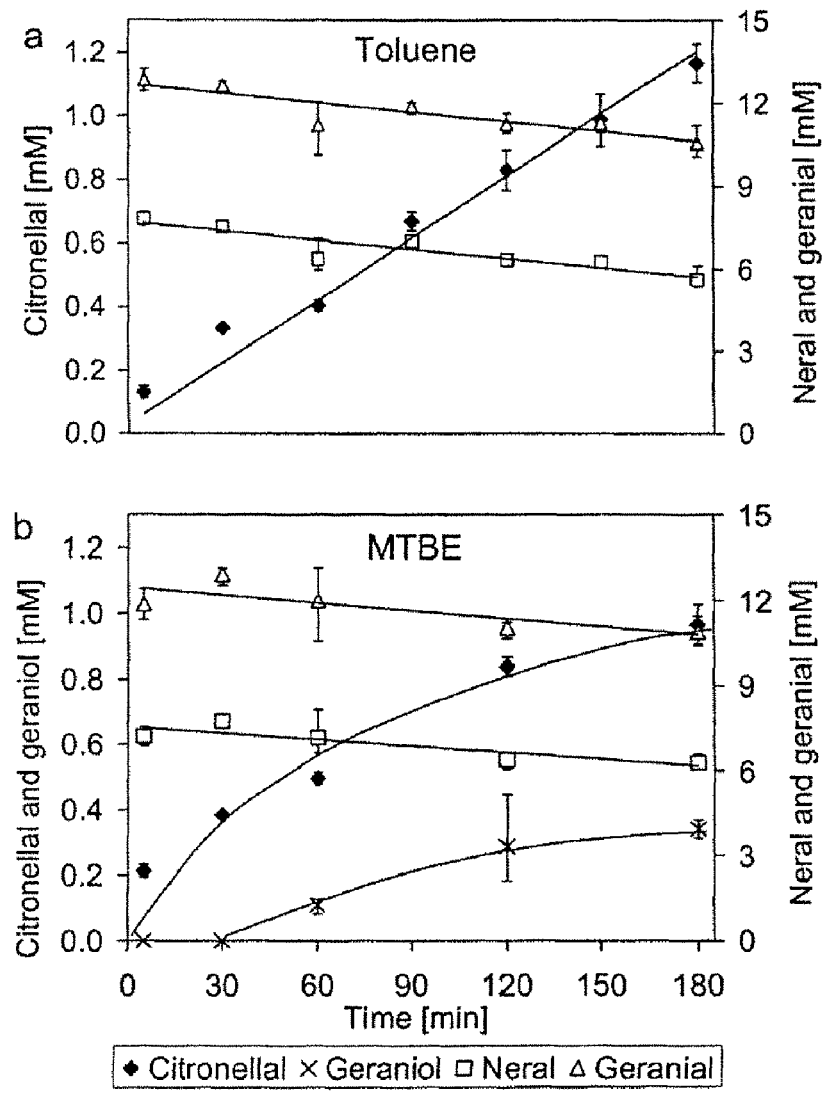
FIG. 4: Citral biotransformation by *Zymomonas mobilis* in the a) aqueous/toluene and b) aqueous/methyl tertiary butylether (MTBE) two-phase systems with NADPH regenerating system (30° C., composition as in FIG. 2 at a biomass concentration of approximately 14 g DCM/l). Average values of three replicates are given and error bars indicate highest and lowest results.

The biotransformations shown in FIGS. 2-4 were carried out as for the two-phase culture screening but with 0.8 ml aqueous phase and 0.2 ml organic solvent in 4 ml screw capped glass vials, magnetically stirred to maintain an emulsion of the organic solvent in the aqueous phase. Details for composition and conditions are given in the respective figure captions. Prior to the start of reaction, 0.5 ml of washed cells at a defined biomass concentration were stirred with 0.15 ml of the respective organic solvent for 30 min on ice. The reaction was started by addition of 0.05 ml of 0.4M citral in the same organic solvent.

Analytical Methods

Concentrations of terpenes were determined by gas chromatography (GC) using a capillary column (Chrompack CP-SIL 5B from Varian, 50 m×0.25 mm, 0.12 μm phase thickness) with nitrogen as carrier gas (0.98 ml/min) and a flame ionization detector (250° C.) with hydrogen (20 ml/min) and air (300 ml/min). The injection volume was 1 μl with a split ratio of 29:1. The injection temperature was 250° C. and the column temperature was held at 100° C. for 9 min and then increased to 240° C. at 50° C./min. Using 1-octanol as an internal standard, terpene concentrations were calculated based on standards which have been subjected to the same extraction procedure as the samples. For the separation of citronellal and isopulegol the initial column temperature was 75° C. for 12 min. Nerol and citronellol were not separated under any of the former conditions. Their separation as well as the chiral analysis was performed with a Supelco Beta Dex 225 column (30 m×0.25 mm, 0.25 μm phase thickness). The split ratio was 1:35, the column flow 2.77 ml/min, the column temperature 95° C. for 35 min, increasing to 160° C. at 5° C./min. Citronellal was identified by co-elution with a citronellal standard from both GC columns.

EXAMPLE 1

Culture Screening in Aqueous Systems 20 yeast strains, 9 strains of filamentous fungi and 17 bacterial strains were tested for citral conversion in three aqueous systems: using whole cells in culture medium or washed and permeabilized cells with NADH or NADPH. Only permeabilized *Zymomonas mobilis* with NADPH formed citronellal. Both, the NADPH regenerating system or direct addition of NADPH supported the citronellal formation. Geraniol was the major product for many of the tested strains, in whole cell cultures as well as with NADH or NADPH addition to permeabilized cells. Also nerol and/or citronellol were formed. Thus the enzyme activities for the reduction of the aldehyde group competed with the required activity for the double-bond reduction.

EXAMPLE 2

Effect of Solvents on Citral Conversion by *Zymomonas mobilis*

*Zymomonas mobilis* was used to test the feasibility of an organic/aqueous two-phase system for the conversion of citral into citronellal. FIG. 2a illustrates citronellal formation in the absence and presence of various water soluble (asterisk) and insoluble solvents, sorted by functionality: two n-alkanes, nine aliphatic alcohols, three ketones, two esters, two ethers, and three aromatic solvents. Four solvents—isoamylalcohol, MTBE, diethylether and toluene—supported approximately ten-fold higher product levels in comparison to the control without any organic solvent. As an additional advantage, most solvents caused decreased levels of the by-products geraniol, nerol and/or citronellol (FIG. 2b). A control experiment, the extraction of geraniol, nerol and citronellol standards, confirmed that their extraction relative to the internal standard was not affected by the presence of e.g. isopropanol, toluene or MTBE in the samples. Therefore decreased by-product levels would have been due to decreased enzymatic reduction of the aldehyde group. Toluene and MTBE were chosen for further experiments.

EXAMPLE 3

Culture Screening in Two-Phase Systems

In the aqueous/toluene screening system citronellal was formed from citral by several strains, which were not identified earlier in the aqueous screening system. For comparison these cultures were adjusted to a similar biomass concentration and citronellal production for the toluene and the MTBE two-phase system is illustrated in FIG. 3. In the toluene system the two bacterial strains achieved at least five-fold higher concentrations of citronellal than the nine eukaryotic strains. In the MTBE system, *Citrobacter freundii* formed less citronellal than in the presence of toluene. A positive result was obtained for *Issatchenkia orientalis*, which did not form citronellal in the toluene system. The addition of 5 mM EDTA resulted in higher citronellal concentrations for most strains but it had an opposite effect for *Citrobacter freundii* and the filamentous fungus *Rhizopus javanicus* (FIG. 3b). Citronellal formation by *Zymomonas mobilis* was unaffected by EDTA.

With respect to by-product formation in the MTBE/EDTA system, the yeast strains and the bacterium *Citrobacter freundii* produced mostly geraniol, some nerol and small amounts of citronellol. In particular, the *Saccharomyces* strains formed up to 13 mM geraniol. Omitting EDTA increased the formation of alcohol by-products for the *Saccharomyces* strains by approximately 10% and for *Zymomonas mobilis* even nine-fold. Isopulegol was not detected in any of the experiments.

The enantiomeric excess (e.e.) values for the product citronellal are listed in table 1. The bacterial enzymes had a preference for forming the (S)-enantiomer with e.e. values of >99% for *Zymomonas mobilis* and 75% for *Citrobacter freundii*. In contrast the yeast strains produced predominantly (R)-citronellal with *Candida rugosa* for example resulting in an e.e. value of more than 98%.

TABLE 1

Enantiomeric excess of citronellal formed by the various strains in the aqueous/MTBE two-phase system containing 5 mM EDTA (FIG. 3b)

| Strain | % e.e. | Enantiomer |
| --- | --- | --- |
| *Zymomonas mobilis* | >99 | (S)- |
| *Citrobacter freundii* | 75 | (S)- |
| *Candida rugosa* | >98 | (R)- |
| *Saccharomyces bayanus* | >97 | (R)- |
| *Saccharomyces cerevisiae* | >96 | (R)- |
| *Kluyveromyces marxianus* | >95 | (R)- |
| *Candida utilis* | >94 | (R)- |
| *Issatchenkia orientalis* | 64 | (R)- |
| *Rhizopus javanicus* | >94 | (R)- |

Citral Biotransformation Profile

FIG. 4 illustrates the profiles of citral biotransformation by *Zymomonas mobilis* in the aqueous/toluene and in the aqueous/MTBE two-phase system. For the former the increase of citronellal concentration continued rather linearly over the three hour period. When the concentration of the NADPH regenerating system was doubled, the same final citronellal concentration was achieved. This indicates that the reaction was not limited by the NADPH regenerating system. Concentrations of both citral isomers, geranial and neral, decreased over time. The alcohols nerol, geraniol and citronellol were not detected. For the aqueous/MTBE two-phase system, citronellal formation was observed to slow over time, though both of the citral isomers, geranial and neral, were consumed linearly over time. Of the alcohol by-products, 0.34 mM of geraniol and less than 0.1 mM of citronellol were formed. The molar balance after 3 h indicated a loss of 16% of the initial substrate in the toluene system and 10% in the MTBE system. In comparison, controls without biomass showed no loss of citral or citronellal over 3 hours. However, controls with boiled biomass lost citral and citronellal to a similar extent as observed in the biotransformations.

EXAMPLE 4

Isolation and Characterization of a Reductase from *Zymomonas mobilis*

Culturing of *Zymomonas mobilis*:

| The cells are grown in a medium composed of | |
| --- | --- |
| Bacto Peptone | 10 g/l |
| Yeast Extract | 10 g/l |
| Glucose*H2O | 20 g/l |
| KH2PO4 | 1 g/l |
| (NH4)2SO4 | 1 g/l |
| MgSO4*7H2O | 0.5 g/l | pH 7.0; sterilization: 20 min 121° C.

For this purpose, in each case 800 ml of medium is introduced into 1 l Erlenmeyer flasks (no baffles) and incubated at 100 rpm and 30° C. for at least 48 hours (usually approx. 65-72 hours). The slight clouding is removed by centrifugation. The biomass yield is low (approx. 2.0-2.5 g/l wet biomass).

Purification of Protein:

Homogenization 106 g of wet biomass are resuspended in 500 ml of disruption buffer (20 mM Tris/HCl, 2 mM EDTA, 10 tablets/l Complete protease inhibitor, pH 8.0), and the pH is corrected with NaOH from pH 6.6 to 7.5. Aliquots of 100 ml of suspension are mixed with 100 ml of glass beads (0.1-0.2 mm in diameter) and disrupted in a ball mill at 5000 rpm for 12 minutes. The glass beads are removed with suction via a G1 glass suction filter and washed. The filtrate (710 ml) is centrifuged at 12 000 rpm (Sorvall, 4 degree C.) for 30 minutes. The supernatant (610 ml, 18.6 mg/ml protein, pH 7.4, conductivity 2.6 mS/cm) is divided into 3 200 ml aliquots and stored at −20 degrees C.

Ion Exchange Chromatography (Q-Sepharose FF)

The homogenate was applied (15 ml/min) to a Q-Sepharose FF chromatography column (diameter 5 cm, volume 400 ml), prewashed with 20 mM Tris/HCl, pH 8.0, 2 mM EDTA, 2 tablets Complete/l (buffer A). For this purpose, the thawed crude homogenate was diluted with buffer A to 500 ml (conductivity 1.6 mS/cm, pH 8.0). After loading, the column was washed with 1000 ml of buffer A (15 ml/min). This was followed by developing with a linear gradient to 100% buffer B (buffer A with 0.5M NaCl, pH 8.0) (1500 ml). A further 750 ml of 100% B were then used for washing. In each case ten 12 ml fractions were combined and assayed.

Hydrophobic Chromatography (TSK-Phenyl)

The fraction of interest from the Q-Sepharose column was used for loading (142 ml, pH 7.0, adjusted to 40% saturation with 32.2 g of ammonium sulfate; 500 mg of protein).

The Phenyl-Sepharose column from Pharmacia was 2.6 cm in diameter, with a volume of 170 ml, and was operated at 10 ml per minute. The column was equilibrated with buffer A, 40% ammonium sulfate saturation, 2 mM EDTA, 2 tablets of Complete/l, 20 mM sodium dihydrogen phosphate pH 7.0. After the loading, the column was washed with buffer A until the base line of absorption was reached. This was followed by developing with a linear gradient to 100% buffer B (buffer A without ammonium sulfate, 3 column volumes). At the end the column was eluted with 2.5 column volumes of buffer C (buffer B with 20% isopropanol). In each case 10 fractions were combined and assayed for activity. Fractions 61 to 70 (92 ml) were collected.

Molecular Sieve Chromatography (Superdex)

The fraction of interest from the Phenylsepharose column (90 ml) was precipitated with 46.4 g of ammonium sulfate (80% saturation) and removed by centrifugation. The pellet was resuspended in running buffer (20 mM sodium phosphate, pH 6.8, 1 tablet of Complete/l, 1 mM EDTA) (9 ml) and applied to the Superdex column, 4 ml/min, 2 min fractions). The active fractions 27 and 28 were collected.

Using this overall procedure, all three homogenates were worked up. 67 ml of fraction of interest containing 18.8 mg of protein in total were obtained.

Affinity Chromatography (Blue Sepharose FF)

A blue Sepharose FF column (diameter 2.6 cm, 50 ml, Pharmacia) was equilibrated in 20 mM sodium dihydrogen phosphate pH 6.8, 1 tablet of Complete/l, 1 mM EDTA. The combined fractions of interest from the molecular sieve chromatography were applied with a flow of 3 ml. The column was then washed with 150 ml of the same buffer, and subsequently with this buffer plus 0.5M NaCl (130 ml). Elution was carried out using the second washing buffer to which in each case 1 mM NADH and NADPH had also been added. Prior to elution with this buffer, the column was incubated in said buffer for 16 hours. Active fractions were collected. The protein does not bind to blue Sepharose under the conditions chosen. However, other proteins were removed in this way, resulting in a successful purification.

Affinity Chromatography (4-hydroxybenzoic Acid Affinity Column)

Preparation of the affinity column: 50 ml of aminohexanoic acid Sepharose are washed with 5 l of water. The filter cake is resuspended in 40 ml of water. 4.2 g of 4-acetoxybenzoic acid (protected hydroxybenzoic acid) are dissolved in 50 ml of DMF and adjusted to pH 4.7 (10 M NaOH). 3.9 g of EDC are dissolved in 10 ml of water and added to the coupling mixture within 15 min. The pH is maintained at 4.7 with HCl. Then another 50 ml of DMF are added and the mixture is agitated at room temperature for 16 hours. The column material is removed with suction via a G2 glass suction filter and washed with 1 l of a 50% water/DMF solution. This is followed by washing with 1 l of water. The column material is then resuspended in 200 ml of cold NaHCO3 solution and 2 ml of acetic anhydride are added. Deprotection is carried out on ice for 90 minutes, resulting in a strong evolution of CO2. The reaction solution is removed with suction and the column material is washed with water. Subsequently, the column material is agitated in a 1M imidazole solution pH 7.9 for 1 hour, then again removed with suction and washed with water and also stored in this state.

The protein does also not bind to this column.

Mono-Q Chromatography

A Mono-Q chromatography column (1 ml Pharmacia) is equilibrated with 20 mM sodium phosphate, pH 7.5, 1 tablet of Complete/l, 1 mM EDTA). 130 ml of the flow-through from the blue Sepharose column (pH 7.5, 2.7 mS/cm) are applied (1 ml/min). The column is then washed with the same buffer. Here too, the protein is already eluted during loading, but contaminations bind to the column.

Hydrophobic Chromatography (Resource-Phenylsepharose, FPLC)

A 1 ml Resource column (Amersham) is equilibrated with 20 mM sodium phosphate, pH 7.0, 2 tablets of Complete/l, 2 mM EDTA, 40% saturation with ammonium sulfate. 140 ml of the flow-through from the Mono-Q-Sepharose column pH 7.5, 2.7 mS/cm) are adjusted with 31.6 g of ammonium sulfate to 40% saturation and applied (160 ml, 1 ml/min). The column is then washed with the same buffer. The column is developed using a linear gradient to the same buffer without ammonium sulfate. Active fractions are collected and developed by SDS gel electrophoresis (FIG. 1). The band at 40 kDa is blotted and N-terminally sequenced.

The purification is summarized in Table 2.

TABLE 2

| Purification step | Total protein | Total activity |
|---|---|---|
| Homogenate | 11.4 g | 6 U |
| Q-Sepharose fraction of interest | 1.5 g | 1 U |
| Phenyl-Sepharose fraction of interest | 471 mg | 2 U |
| Superdex fraction of interest | 18.8 mg | 1 U |
| Blue Sepharose fraction of interest | 3 mg | 0.74 U |
| Mono Q fraction of interest | 2 mg | 0.7 U |
| Resource Phenyl fraction of interest | 1 mg | 0.5 U |

Sequencing of the N Terminus

The following N-terminal sequence was obtained:
PSLFDPIRFGAFTAKNRIWMAPLTRGR (SEQ ID No. 1)

A computer search with this identified N-terminal peptide in the published genome of *Zymomonas mobilis* (Seo J. S et al. "The genome sequence of the ethanologenic bacterium *Zymomonas mobilis* ZM4", Nat. Biotechnol. 23:63-68 (2005), EMBL AE008692) identified the protein as NADH flavin oxidoreductase with 358 aminoacids and a molecular weight of 39489 Dalton (EMBL AE008692, AAV90509.1, primary accession number Q5NLA1.

REFERENCES

[1] W. A. M. Wolken, M. J. van der Werf, Appl. Microbiol. Biotechnol. 57 (2001) 731.
[2] B. Stumpf, K. Kieslich, Appl. Microbiol. Biotechnol. 34 (1991) 598.
[3] W. A. M. Wolken, W. J. V. Van Loo, J. Tramper, M. J. van der Werf, Eur. J. Biochem. 269 (2002) 5903.
[4] W. A. M. Wolken, R. ten Have, M. J. van der Werf, J. Agric. Food Chem. 48 (2000) 5401.
[5] A. F. Trasarti, A. J. Marchi, C. R. Apesteguia, J. Catal. 224 (2004) 484.
[6] P. Mäki-Arvela, N. Kumar, D. Kubicka, A. Nasir, T. Heikkilä, V. P. Lehto, R. Sjoholm, T. Salmi, D. Y. Murzin, J. Mol. Cat. A: Chem 240 (2005) 72.
[7] R. E. Williams, N. C. Bruce, Microbiology 148 (2002) 1607.
[8] M. J. van der Werf, A. M. Boot, Microbiology 146 (2000) 1129.
[9] R. León, P. Fernandes, H. M. Pinheiro, J. M. S. Cabral, Enzyme Microb. Technol. 23 (1998) 483.
[10] M. Decleire, W. De Cat, N. Van Huynh, Enzyme Microb. Technol. 9 (1987) 300.
[11] U. H. Chun, P. L. Rogers, Appl. Microbiol. Biotechnol. 29 (1988) 19.
[12] H. J. P. Marvin, M. B. A. Ter Beest, B. Witholt, J. Bacteriol. 171 (1989) 5262.
[13] K. Kitzing, T. B. Fitzpatrick, C. Wilken, J. Sawa, G. P. Bourenkov, P. Macheroux, T. Clausen, J. Biol. Chem. 280 (2005) 27904.
[14] A. D. N. Vaz, S. Chakraborty, V. Massey, Biochemistry 34 (1995) 4246.
[15] K. Stott, K. Saito, D. J. Thiele, V. Massey, 268 (1993) 6097.
[16] J. S. Seo, H. Chong, H. S. Park, K. O. Yoon, C. Jung, J. J. Kim, J. H. Hong, H. Kim, J. H. Kim, J. I. Kil, C. J. Park, H. M. Oh, J. S. Lee, S. J. Jin, H. W. Urn, H. J. Lee, S. J. Oh, J. Y. Kim, H. L. Kang, S. Y. Lee, K. J. Lee, H. S. Kang, Nature Biotechnol. 23 (2005) 63.

The invention claimed is:

1. A process for producing optically active Citronellal comprising enzymatically reducing Citral in a two-phase liquid system with a reductase from a microorganism selected from the group consisting of *Zymomonas mobilis, Citrobacter freundii, Candida rugosa, Saccharomyces bayanus, Saccharomyces cerevisiae, Kluyveromyces marxianus, Candida utilis, Issatchenkia orientalis,* and *Rhizopus javanicus.*

2. The process of claim 1, wherein the reductase is from a microorganism selected from the group consisting of *Zymomonas mobilis* and *Citrobacter freundii.*

3. The process of claim 1, wherein the reductase is from a microorganism selected from the group consisting of *Candida rugosa, Saccharomyces bayanus, Saccharomyces cerevisiae, Kluyveromyces marxianus, Candida utilis, Issatchenlda orientalis,* and *Rhizopus javanicus.*

4. The process of claim 1, wherein said two-phase liquid system comprises methyl tert-butyl ether (MTBE) and water.

5. The process of claim 1, wherein one phase of said two-phase liquid system is a buffered aqueous solution.

6. The process of claim 1, wherein said reductase is coupled to an NADPH regenerating system.

* * * * *